United States Patent
Hirai et al.

(10) Patent No.: US 7,524,986 B2
(45) Date of Patent: Apr. 28, 2009

(54) METHODS FOR PRODUCING AROMATIC CARBOXYLIC ACIDS

(75) Inventors: Naruhisa Hirai, Himeji (JP); Masahiko Terada, Himeji (JP)

(73) Assignee: Daicel Chemical Industries, Ltd., Osaka-shi (JP)

( * ) Notice: Subject to any disclaimer, the term of this patent is extended or adjusted under 35 U.S.C. 154(b) by 0 days.

(21) Appl. No.: 10/594,212

(22) PCT Filed: Feb. 23, 2005

(86) PCT No.: PCT/JP2005/003434

§ 371 (c)(1),
(2), (4) Date: Sep. 26, 2006

(87) PCT Pub. No.: WO2005/100294

PCT Pub. Date: Oct. 27, 2005

(65) Prior Publication Data

US 2007/0191634 A1    Aug. 16, 2007

(30) Foreign Application Priority Data

Apr. 8, 2004    (JP) .............................. 2004-114643

(51) Int. Cl.
  *C07C 51/16*    (2006.01)
(52) U.S. Cl. ...................... 562/412; 562/413
(58) Field of Classification Search ................. 562/412, 562/413
  See application file for complete search history.

(56) References Cited

U.S. PATENT DOCUMENTS

| | | | |
|---|---|---|---|
| 6,034,269 | A | 3/2000 | Turner et al. |
| 6,307,099 | B1 | 10/2001 | Turner et al. |
| 2005/0020439 | A1 | 1/2005 | Ishii et al. |

FOREIGN PATENT DOCUMENTS

| | | | |
|---|---|---|---|
| EP | 1459804 A1 | * | 9/2004 |
| JP | 8-38909 A | | 2/1996 |
| JP | 9-327626 | | 12/1997 |
| JP | 2001-513102 A | | 8/2001 |
| JP | 2001-253838 A | | 9/2001 |
| JP | 2002-128726 A | | 5/2002 |
| JP | 2002-522406 A | | 7/2002 |
| JP | 2003-128618 A | | 5/2003 |
| JP | 2003128618 A | * | 5/2003 |
| WO | WO-03/028884 A1 | | 4/2003 |
| WO | WO-03/055600 A1 | | 7/2003 |

\* cited by examiner

*Primary Examiner*—Jafar Parsa
(74) *Attorney, Agent, or Firm*—Birch, Stewart, Kolasch & Birch, LLP

(57) ABSTRACT

A method of this invention produces an aromatic carboxylic acid, by oxidizing an aromatic compound B with oxygen in the presence of a catalytic nitrogen-containing cyclic compound A to thereby yield a corresponding aromatic carboxylic acid, the aromatic compound B having one or more hydrocarbon groups alone as substituents on its aromatic ring, and the catalytic nitrogen-containing cyclic compound A having a skeleton represented by following Formula (i):

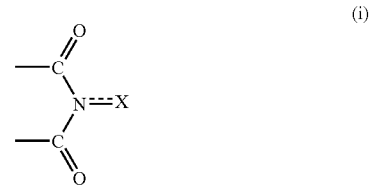

wherein X represents oxygen atom or an —OR group, and wherein R represents hydrogen atom or a hydroxyl-protecting group, as a constitutive member of its ring. The method includes the step of carrying out a reaction at a concentration of the aromatic compound B in the reaction system of 3.0 percent by weight or less, while continuously feeding the catalytic nitrogen-containing cyclic compound A, the aromatic compound B, a reaction solvent, and oxygen to a reactor and continuously extracting a reaction mixture from the reactor. This method can produce aromatic carboxylic acids with industrially good productivity without the need for special reaction facilities and without undergoing many steps.

8 Claims, No Drawings

METHODS FOR PRODUCING AROMATIC CARBOXYLIC ACIDS

TECHNICAL FIELD

The present invention relates to methods for producing aromatic carboxylic acids that are useful typically as raw materials for polyamides and polyesters and intermediates for fine chemicals. More specifically, it relates to methods of oxidizing an aromatic compound having a hydrocarbon group, such as an alkyl group, on its aromatic ring with oxygen in the presence of a catalyst to produce a corresponding aromatic carboxylic acid.

BACKGROUND ART

Methods for producing aromatic carboxylic acids include a method of oxidizing an aromatic compound having an alkyl group on its aromatic ring, such as xylene, with molecular oxygen in an organic acid in the presence of a Co—Mn—Br catalyst. This method, however, uses highly corrosive bromine and must thereby use production facilities of special materials.

Japanese Unexamined Patent Application Publication (JP-A) No. Hei 08-38909 and JP-A No. Hei 09-327626 propose oxidation catalysts comprising an imide compound having a specific structure or those comprising the imide compound and a transition metallic compound as catalysts for oxidizing substrates with molecular oxygen. These catalysts enable oxidation of an alkyl group bound to an aromatic ring under mild conditions. PCT International Publication Number WO 03/28884 and JP-A No. 2003-128618 each disclose a method of oxidizing an aromatic compound having an alkyl group or a lower-order oxidized group thereof on its aromatic ring with oxygen in the presence of a catalyst comprising an imide compound having a N-substituted cyclic imide skeleton to thereby yield a corresponding aromatic carboxylic acid. This method can produce an aromatic carboxylic acid without the need for special reaction facilities. Even this method, however, is still industrially insufficient in production conditions and productivity.

DISCLOSURE OF INVENTION

Accordingly, an object of the present invention is to provide a method for producing an aromatic carboxylic acid with good industrial productivity without the need for special reaction facilities and without undergoing many steps.

Another object of the present invention is to provide a method for producing an aromatic carboxylic acid, which enables efficient use of a catalyst.

Yet another object of the present invention is to provide a method for producing an aromatic carboxylic acid, which can maintain the activity of a catalyst over a long term.

Another object of the present invention is to provide a method for efficiently producing an aromatic polycarboxylic acid with simple facilities.

After intensive investigations to achieve the above objects, the present inventors have found that an aromatic carboxylic acid can be produced with good industrial productivity by carrying out a reaction according to a continuous gas-liquid reaction system, in which a specific catalytic nitrogen-containing cyclic compound, an aromatic compound having a hydrocarbon group bound to its aromatic ring, a solvent, and oxygen are continuously fed to a reactor, and a reaction mixture is continuously extracted from the reactor; and carrying out the reaction at a concentration of the aromatic compound in the reaction system at a specific level or below. The present invention has been achieved based on these findings.

Specifically, the present invention provides a method for producing an aromatic carboxylic acid, by oxidizing an aromatic compound B with oxygen in the presence of a catalytic nitrogen-containing cyclic compound A to thereby yield a corresponding aromatic carboxylic acid, the aromatic compound B having one or more hydrocarbon groups alone as substituents on its aromatic ring, and the catalytic nitrogen-containing cyclic compound A having a skeleton represented by following Formula (i):

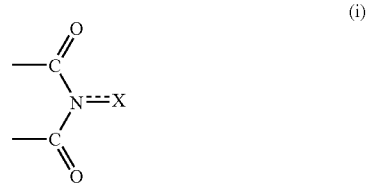

wherein X represents oxygen atom or an —OR group, and wherein R represents hydrogen atom or a hydroxyl-protecting group, as a constitutive member of its ring, the method comprising the step of carrying out a reaction at a concentration of the aromatic compound B in the reaction system of 3.0 percent by weight or less, while continuously feeding the catalytic nitrogen-containing cyclic compound A, the aromatic compound B, a reaction solvent, and oxygen to a reactor and continuously extracting a reaction mixture from the reactor.

The reaction in the production method is preferably carried out at a molar ratio of the catalytic nitrogen-containing cyclic compound A to the aromatic compound B in the reaction system of 0.01 or more. The reaction temperature is preferably 150° C. or higher. The oxygen concentration of an offgas is preferably controlled at 1% to 8%, and the residence time is preferably in the range of 0.5 to 4 hours.

According to an embodiment of the production method, the reaction is continuously carried out using plural reactors arranged in series and is carried out, at least in the downstreammost reactor, at a concentration of the aromatic compound B in the reaction system of 3.0 percent by weight or less.

The catalytic nitrogen-containing cyclic compound A includes a cyclic imide compound having a cyclic imide skeleton represented by following Formula (I):

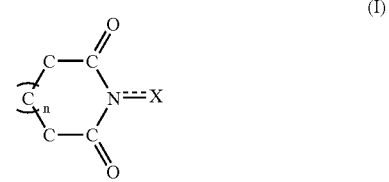

wherein "n" denotes 0 or 1; and X represents oxygen atom or an —OR group, wherein R represents hydrogen atom or a hydroxyl-protecting group, and a cyclic acylurea compound having a cyclic acylurea skeleton represented by following Formula (II):

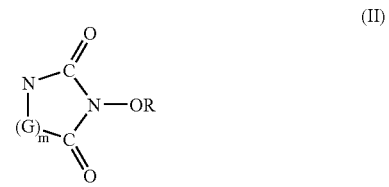

wherein "m" denotes 1 or 2; G represents carbon atom or nitrogen atom, wherein, when m is 2, two Gs may be the same as or different from each other; and R is as defined above.

The production method preferably uses a metallic compound as a promoter. The metallic compound used herein is preferably at least one compound selected from the group consisting of cobalt compounds and manganese compounds. The amount of the metallic compound is preferably in the range of 0.001 to 10 moles per 1 mole of the catalytic nitrogen-containing cyclic compound A.

The present invention eliminates the need for using highly corrosive reagents and can thereby efficiently produce aromatic carboxylic acids without using special reaction facilities. It employs a continuous gas-liquid reaction system (flow reaction system), carries out a reaction at a very low concentration of the substrate in the reaction system, and can thereby produce aromatic carboxylic acids with high production efficiency. This is probably because the catalyst can stably exhibit its action. In addition, the present invention can efficiently utilize the catalyst. The present invention is particularly advantageous in the production of aromatic polycarboxylic acids such as terephthalic acid.

BEST MODE FOR CARRYING OUT THE INVENTION

[Catalytic Nitrogen-containing Cyclic Compound A]

A nitrogen-containing cyclic compound having the skeleton represented by Formula (i) as a constitutive member of its ring is used as a catalyst in the present invention.

The bond between the nitrogen atom and X in Formula (i) is a single bond or a double bond. The nitrogen-containing cyclic compound may have a plurality of the skeletons represented by Formula (i) per molecule. When X is an —OR group and R is a hydroxyl-protecting group, the nitrogen-containing cyclic compound may comprise plural moieties which correspond to the skeleton represented by Formula (i) except for R and are combined through R.

Conventional hydroxyl-protecting groups in the field of organic synthesis can be used as the hydroxyl-protecting group represented by R in Formula (i). Examples of such protecting groups are alkyl groups including $C_{1-4}$ alkyl groups such as methyl and t-butyl groups; alkenyl groups such as allyl group; cycloalkyl groups such as cyclohexyl group; aryl groups such as 2,4-dinitrophenyl group; and aralkyl groups such as benzyl, 2,6-dichlorobenzyl, 3-bromobenzyl, 2-nitrobenzyl, and triphenylmethyl groups. Examples of the protecting groups also include groups capable of forming an acetal or hemi-acetal group with hydroxyl group, including substituted methyl groups such as methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups; substituted ethyl groups such as 1-ethoxyethyl, 1-methyl-1-methoxyethyl, 1-isopropoxyethyl, 2,2,2-trichloroethyl, and 2-methoxyethyl groups; tetrahydropyranyl group; tetrahydrofuranyl group; 1-hydroxyalkyl groups such as 1-hydroxyethyl, 1-hydroxyhexyl, 1-hydroxydecyl, 1-hydroxyhexadecyl, and 1-hydroxy-1-phenylmethyl groups. They also include acyl groups (including aliphatic saturated or unsaturated acyl groups including aliphatic $C_{1-20}$ acyl groups such as formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, and stearoyl groups; acetoacetyl group; alicyclic acyl groups including cycloalkanecarbonyl groups such as cyclopentanecarbonyl and cyclohexanecarbonyl groups; and aromatic acyl groups such as benzoyl and naphthoyl group); sulfonyl groups such as methanesulfonyl, ethanesulfonyl, trifluoromethanesulfonyl, benzenesulfonyl, p-toluenesulfonyl, and naphthalenesulfonyl groups; alkoxycarbonyl groups including ($C_{1-4}$ alkoxy)-carbonyl groups such as methoxycarbonyl, ethoxycarbonyl, and t-butoxycarbonyl groups; aralkyloxycarbonyl groups such as benzyloxycarbonyl group and p-methoxybenzyloxycarbonyl group; substituted or unsubstituted carbamoyl groups such as carbamoyl, methylcarbamoyl, and phenylcarbamoyl groups; groups derived from inorganic acids (e.g., sulfuric acid, nitric acid, phosphoric acid, and boric acid) by removal of OH group; dialkylphosphinothioyl groups such as dimethylphosphinothioyl group; diarylphosphinothioyl groups such as diphenylphosphinothioyl group; and substituted silyl groups such as trimethylsilyl, t-butyldimethylsilyl, tribenzylsilyl, and triphenylsilyl groups.

When X is an —OR group, and a plurality of moieties (N-oxy cyclic imide skeleton) each corresponding to the skeleton represented by Formula (i) except for R are combined through R, examples of R include acyl groups derived from polycarboxylic acids, such as oxalyl, malonyl, succinyl, glutaryl, adipoyl, phthaloyl, isophthaloyl, and terephthaloyl groups; carbonyl group; polyvalent hydrocarbon groups such as methylene, ethylidene, isopropylidene, cyclopentylidene, cyclohexylidene, and benzylidene groups, of which groups that form an acetal bond with two hydroxyl groups are preferred.

Preferred examples of R include hydrogen atom; groups capable of forming an acetal or hemi-acetal group with hydroxyl group; and hydrolyzable protecting groups that can be removed or deprotected as a result of hydrolysis. The hydrolyzable protecting groups include groups derived from acids by removal of OH group, such as acyl groups, sulfonyl groups, alkoxycarbonyl groups, and carbamoyl groups. Examples of the acids herein are carboxylic acids, sulfonic acid, carbonic acid, carbamic acid, sulfuric acid, phosphoric acid, and boric acid.

The nitrogen-containing cyclic compounds include, for example, cyclic imide compounds having the N-substituted cyclic imide skeleton represented by Formula (I). The cyclic imide compounds may each have a plurality of the N-substituted cyclic imide skeletons represented by Formula (I) per molecule. When X is an —OR group and R is a hydroxyl-protecting group, the cyclic imide compounds may have a plurality of moieties (N-oxy cyclic imide skeletons) which correspond to the N-substituted cyclic imide skeleton except for R and are combined through R.

In Formula (I), "n" denotes 0 or 1. Specifically, Formula (I) represents a N-substituted cyclic imide skeleton having five members when "n" is 0, and represents a N-substituted cyclic imide skeleton having six members when "n" is 1.

Representative examples of the cyclic imide compounds include compounds represented by following Formula (1):

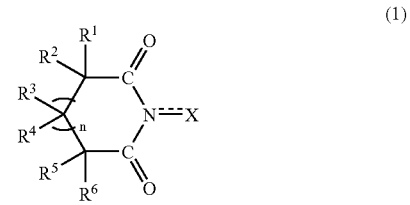

wherein "n" denotes 0 or 1; X represents oxygen atom or an —OR group, wherein R represents hydrogen atom or a hydroxyl-protecting group; and $R^1$, $R^2$, $R^3$, $R^4$, $R^5$ and $R^6$ are the same as or different from one another and each represent hydrogen atom, a halogen atom, an alkyl group, an aryl group, a cycloalkyl group, hydroxyl group, an alkoxy group, carboxyl group, a substituted oxycarbonyl group, an acyl group, or an acyloxy group, wherein at least two of $R^1$, $R^2$, $R^3$, $R^4$, $R^5$, and $R^6$ may be combined to form one of a double bond, an aromatic ring, and a non-aromatic ring with carbon atom or carbon-carbon bond constituting the cyclic imide skeleton, and wherein one or more N-substituted cyclic imide groups represented by following Formula (a):

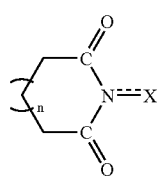

(a)

wherein "n" and X are as defined above,
may be formed on $R^1$, $R^2$, $R^3$, $R^4$, $R^5$, and $R^6$ or on the double bond or the aromatic or non-aromatic ring formed by at least two of $R^1$, $R^2$, $R^3$, $R^4$, $R^5$, and $R^6$.

Of the substituents $R^1$, $R^2$, $R^3$, $R^4$, $R^5$ and $R^6$ in the imide compounds represented by Formula (1), the halogen atoms include iodine, bromine, chlorine, and fluorine atoms. The alkyl groups include straight- or branched-chain alkyl groups having about one to about thirty carbon atoms, such as methyl, ethyl, propyl, isopropyl, butyl, isobutyl, s-butyl, t-butyl, hexyl, decyl, dodecyl, tetradecyl, and hexadecyl groups, of which those having about one to about twenty carbon atoms are preferred.

The aryl groups include phenyl, tolyl, xylyl, and naphthyl groups, and the cycloalkyl groups include cyclopentyl and cyclohexyl groups. Examples of the alkoxy groups include alkoxy groups having about one to about thirty carbon atoms, such as methoxy, ethoxy, isopropoxy, butoxy, t-butoxy, hexyloxy, octyloxy, decyloxy, dodecyloxy, tetradecyloxy, and octadecyloxy groups, of which those having about one to about twenty carbon atoms are preferred.

The substituted oxycarbonyl groups include ($C_{1-30}$ alkoxy)-carbonyl groups such as methoxycarbonyl, ethoxycarbonyl, isopropoxycarbonyl, butoxycarbonyl, t-butoxycarbonyl, hexyloxycarbonyl, decyloxycarbonyl, and hexadecyloxycarbonyl groups, of which ($C_{1-20}$ alkoxy)-carbonyl groups are preferred; cycloalkyloxycarbonyl groups such as cyclopentyloxycarbonyl and cyclohexyloxycarbonyl groups, of which 3- to 20-membered cycloalkyloxycarbonyl groups are preferred; aryloxycarbonyl groups such as phenyloxycarbonyl, and naphthyloxycarbonyl groups, of which ($C_{6-20}$ aryloxy)-carbonyl groups are preferred; and aralkyloxycarbonyl groups such as benzyloxycarbonyl group, of which ($C_{7-21}$ aralkyloxy)-carbonyl groups are preferred.

Examples of the acyl groups include aliphatic saturated or unsaturated acyl groups including aliphatic $C_{1-30}$ acyl groups such as formyl, acetyl, propionyl, butyryl, isobutyryl, valeryl, pivaloyl, hexanoyl, octanoyl, decanoyl, lauroyl, myristoyl, palmitoyl, and stearoyl groups, of which aliphatic $C_{1-20}$ acyl groups are preferred; acetoacetyl group; alicyclic acyl groups including cycloalkanecarbonyl groups such as cyclopentanecarbonyl, and cyclohexanecarbonyl groups; and aromatic acyl groups such as benzoyl and naphthoyl groups.

Examples of the acyloxy groups include aliphatic saturated or unsaturated acyloxy groups including aliphatic $C_{1-30}$ acyloxy groups such as formyloxy, acetyloxy, propionyloxy, butyryloxy, isobutyryloxy, valeryloxy, pivaloyloxy, hexanoyloxy, octanoyloxy, decanoyloxy, lauroyloxy, myristoyloxy, palmitoyloxy, and stearoyloxy groups, of which aliphatic $C_{1-20}$ acyloxy groups are preferred; acetoacetyloxy group; alicyclic acyloxy groups including cycloalkanecarbonyloxy groups such as cyclopentanecarbonyloxy and cyclohexanecarbonyloxy groups; and aromatic acyloxy groups such as benzoyloxy and naphthoyloxy groups.

The substituents $R^1$, $R^2$, $R^3$, $R^4$, $R^5$ and $R^6$ may be the same as or different from one another. At least two of $R^1$, $R^2$, $R^3$, $R^4$, $R^5$ and $R^6$ in Formula (1) may be combined to form one of a double bond, an aromatic ring, and a non-aromatic ring with carbon atom or carbon-carbon bond constituting the cyclic imide skeleton. The aromatic or non-aromatic ring is preferably a ring having about five to about twelve members, and more preferably a ring having about six to about ten members. It may be a heterocyclic ring or a fused heterocyclic ring but is often a hydrocarbon ring. Examples of such rings include non-aromatic alicyclic rings including substituted or unsubstituted cycloalkane rings such as cyclohexane ring, and substituted or unsubstituted cycloalkene rings such as cyclohexene ring; non-aromatic bridged rings including substituted or unsubstituted bridged hydrocarbon rings such as 5-norbornene ring; and substituted or unsubstituted aromatic rings (including fused rings) such as benzene ring and naphthalene ring. The ring often comprises an aromatic ring. The ring may have one or more substituents such as alkyl groups, haloalkyl groups, hydroxyl group, alkoxy groups, carboxyl group, substituted oxycarbonyl groups, acyl groups, acyloxy groups, nitro group, cyano group, amino group, and halogen atoms.

One or more of the N-substituted cyclic imide groups represented by Formula (a) may be further formed on $R^1$, $R^2$, $R^3$, $R^4$, $R^5$, $R^6$, or on the double bond or the aromatic or non-aromatic ring formed by at least two of $R^1$, $R^2$, $R^3$, $R^4$, $R^5$, and $R^6$. For example, when $R^1$, $R^2$, $R^3$, $R^4$, $R^5$ or $R^6$ is an alkyl group having two or more carbon atoms, the formed N-substituted cyclic imide group may be formed as including two adjacent carbon atoms constituting the alkyl group. When at least two of $R^1$, $R^2$, $R^3$, $R^4$, $R^5$ and $R^6$ are combined to form a double bond with a carbon-carbon bond constituting the cyclic imide skeleton, the N-substituted cyclic imide group may be formed as including the double bond. When at least two of $R^1$, $R^2$, $R^3$, $R^4$, $R^5$ and $R^6$ are combined to form an aromatic or non-aromatic ring with carbon atom or carbon-carbon bond constituting the cyclic imide skeleton, the N-substituted cyclic imide group may be formed as including two adjacent carbon atoms constituting the ring.

Preferred imide compounds include compounds represented by following Formulae:

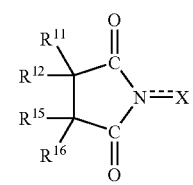

(1a)

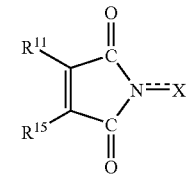

(1b)

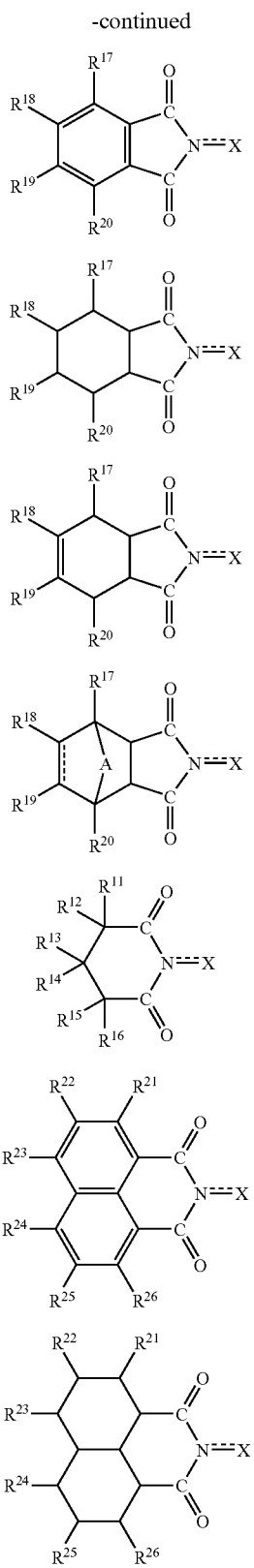

wherein $R^{11}$ to $R^{16}$ are the same as or different from one another and each represent hydrogen atom, a halogen atom, an alkyl group, an aryl group, a cycloalkyl group, hydroxyl group, an alkoxy group, carboxyl group, a substituted oxycarbonyl group, an acyl group, or an acyloxy group; $R^{17}$ to $R^{26}$ are the same as or different from one another and each represent hydrogen atom, an alkyl group, a haloalkyl group, hydroxyl group, an alkoxy group, carboxyl group, a substituted oxycarbonyl group, an acyl group, an acyloxy group, nitro group, cyano group, amino group, or a halogen atom, wherein adjacent two of $R^{17}$ to $R^{26}$ may be combined to form the five- or six-membered N-substituted cyclic imide skeleton in Formula (1c), (1d), (1e), (1f), (1h) or (1i); "A" in Formula (1f) represents methylene group or oxygen atom; and X is as defined above.

The halogen atoms, alkyl groups, aryl groups, cycloalkyl groups, hydroxyl group, alkoxy groups, carboxyl group, substituted oxycarbonyl groups, acyl groups, and acyloxy groups as the substituents $R^{11}$ to $R^{16}$ are as with the corresponding groups exemplified in $R^1$ to $R^6$.

Of the substituents $R^{17}$ to $R^{26}$, the alkyl groups include those as with above, of which alkyl groups having about one to about six carbon atoms are preferred; the haloalkyl groups include haloalkyl groups having about one to about four carbon atoms, such as trifluoromethyl group; the alkoxy groups include those as with above, of which lower alkoxy groups having about one to about four carbon atoms are preferred; and the substituted oxycarbonyl groups include those as with above, such as alkoxycarbonyl groups, cycloalkyloxycarbonyl groups, aryloxycarbonyl groups, and aralkyloxycarbonyl groups. The acyl groups include those as with above, such as saturated or unsaturated aliphatic acyl groups, acetoacetyl group, alicyclic acyl groups, and aromatic acyl groups; the acyloxy groups include those as with above, such as saturated or unsaturated aliphatic acyloxy groups, acetoacetyloxy group, alicyclic acyloxy groups, and aromatic acyloxy groups. Examples of the halogen atoms are fluorine, chlorine, and bromine atoms. The substituents $R^{17}$ to $R^{26}$ are each often one of hydrogen atom, a lower alkyl group having about one to about four carbon atoms, carboxyl group, a substituted oxycarbonyl group, nitro group, and a halogen atom.

Of preferred imide compounds, representative examples of compounds having a five-membered N-substituted cyclic imide skeleton include compounds having a cyclic imide skeleton of Formula (1) wherein X is an —OR group and R is a hydrogen atom, such as N-hydroxysuccinimide, N-hydroxy-α-methylsuccinimide, N-hydroxy-α,α-dimethylsuccinimide, N-hydroxy-α,β-dimethylsuccinimide, N-hydroxy-α,α,β,β-tetramethylsuccinimide, N-hydroxymaleimide, N-hydroxyhexahydrophthalimide, N,N'-dihydroxycyclohexanetetracarboxylic diimide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitic diimide, N,N'-dihydroxynaphthalenetetracarboxylic diimide, α,β-diacetoxy-N-hydroxysuccinimide, N-hydroxy-α,β-bis(propionyloxy)succinimide, N-hydroxy-α,β-bis(valeryloxy)succinimide, N-hydroxy-α,β-bis(lauroyloxy)succinimide, α,β-bis(benzoyloxy)-N-hydroxysuccinimide, N-hydroxy-4-methoxycarbonylphthalimide, 4-chloro-N-hydroxyphthalimide, 4-ethoxycarbonyl-N-hydroxyphthalimide, N-hydroxy-4-pentyloxycarbonylphthalimide, 4-dodecyloxy-N-hydroxycarbonylphthalimide, N-hydroxy-4-phenoxycarbonylphthalimide, N-hydroxy-4,5-bis(methoxycarbonyl)phthalimide, 4,5-bis(ethoxycarbonyl)-N-hydroxyphthalimide, N-hydroxy-4,5-bis(pentyloxycarbonyl)phthalimide, 4,5-bis(dodecyloxycarbonyl)-N-hydroxyphthalimide, and N-hydroxy-4,5-bis(phenoxycarbonyl)phthalimide; compounds corresponding to these compounds, except with R being an acyl group such as acetyl group, propionyl group, or benzoyl group; compounds having a cyclic imide skeleton of Formula (1) wherein X is an —OR group and R is a group capable of forming an acetal or hemi-acetal bond with hydroxyl group, such as N-methoxymethyloxyphthalimide, N-(2-methoxyethoxymethyloxy)phthalimide, and N-tetrahydropyranyloxyphthalimide; compounds wherein X is an —OR group and R is sulfonyl group, such as N-methanesulfonyloxyphthalimide and N-(p-toluenesulfonyloxy)phthalimide; and compounds having a cyclic imide skeleton of Formula (1) wherein X is an —OR group and R is a group derived from an inorganic acid by removal of OH group, such as sulfate, nitrate, phosphate or borate of N-hydroxyphthalimide.

Of preferred imide compounds, representative examples of compounds having a six-membered N-substituted cyclic imide skeleton include compounds having a cyclic imide skeleton of Formula (1) wherein X is an —OR group and R is hydrogen atom, such as N-hydroxyglutarimide, N-hydroxy-α,α-dimethylglutarimide, N-hydroxy-β,β-dimethylglutarimide, N-hydroxy-1,8-decalindicarboximide, N,N'-dihydroxy-1,8;4,5-decalintetracarboxylic diimide, N-hydroxy-1,8-naphthalenedicarboximide (N-hydroxynaphthalimide), and N,N'-dihydroxy-1,8;4,5-naphthalenetetracarboxylic diimide; compounds corresponding to these compounds, except with R being an acyl group such as acetyl group, propionyl group, or benzoyl group; compounds having a cyclic imide skeleton of Formula (1) wherein X is an —OR group and R is a group capable of forming an acetal or hemi-acetal bond with hydroxyl group, such as N-methoxymethyloxy-1,8-naphthalenedicarboximide and N,N'-bis(methoxymethyloxy)-1,8;4,5-naphthalenetetracarboxylic diimide; compounds having a cyclic imide skeleton of Formula (1) wherein X is an —OR group and R is sulfonyl group, such as N-methanesulfonyloxy-1,8-naphthalenedicarboximide and N,N'-bis(methanesulfonyloxy)-1,8;4,5-naphthalenetetracarboxylic diimide; and compounds having a cyclic imide skeleton of Formula (1) wherein X is an —OR group and R is a group derived from an inorganic acid by removal of OH group, such as sulfate, nitrate, phosphate or borate of N-hydroxy-1,8-naphthalenedicarboximide or N,N'-dihydroxy-1,8;4,5-naphthalenetetracarboxylic diimide.

The nitrogen-containing cyclic compounds further include cyclic acylurea compounds having the cyclic acylurea skeleton represented by Formula (II) [—C(=O)—N—C(=O)—N—], in addition to the cyclic imide compounds. The cyclic acylurea compounds may each have a plurality of the cyclic acylurea skeletons represented by Formula (II) per molecule. The cyclic acylurea compounds may each comprise a plurality of moieties (N-oxy cyclic acylurea skeleton) combined through R, which moieties correspond to the cyclic acylurea skeleton represented by Formula (II), except for R. The atom G and the nitrogen atom combined with G constituting the cyclic acylurea skeleton may have at least one substituent. The cyclic acylurea skeleton may further have a non-aromatic or aromatic ring fused therewith and/or may have a double bond in its ring.

The cyclic acylurea skeletons represented by Formula (II) include a 3-hydroxy (or 3-substituted oxy)-hydantoin skeleton represented by following Formula (IIa); a 4-hydroxy- (or 4-substituted oxy)-1,2,4-triazolidine-3,5-dione skeleton [inclusive of a 4-hydroxy (or 4-substituted oxy)-1,2,4-triazoline-3,5-dione skeleton]] represented by following Formula (IIb); a hydro-3-hydroxy (or 3-substituted oxy)-1,3-diazine-2,4-dione skeleton [inclusive of a hexahydro-1-hydroxy (or 1-substituted oxy)-1,3-diazine-2,4,6-trione skeleton, a hexahydro-1,3-dihydroxy (or 1,3-bis-substituted oxy)-1,3-diazine-2,4,6-trione skeleton, and a 3-hydroxy (or 3-substituted oxy) uracil skeleton] represented by following Formula (IIc); a hydro-4-hydroxy (or 4-substituted oxy)-1,2,4-triazine-3,5-dione skeleton represented by following Formula (IId); a hydro-1-hydroxy (or 1-substituted oxy)-1,3,5-triazine-2,6-dione skeleton represented by following Formula (IIe); and a hydro-5-hydroxy (or 5-substituted oxy)-1,2,3,5-tetrazine-4,6-dione skeleton represented by following Formula (IIf):

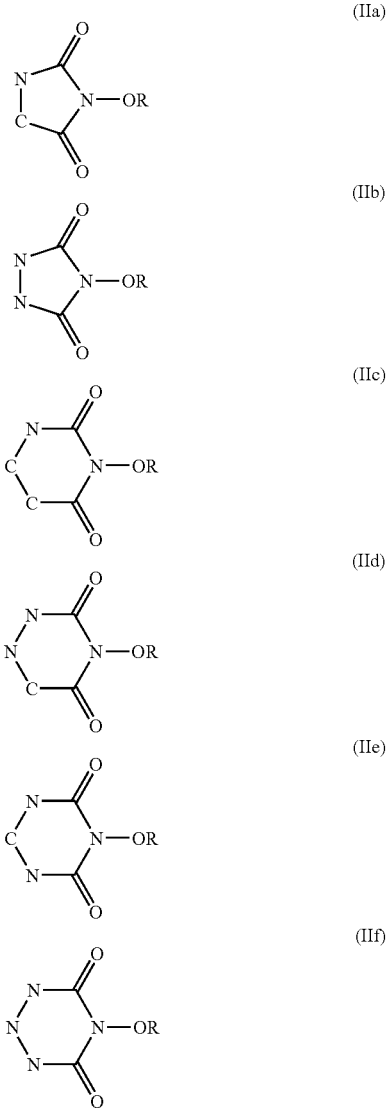

wherein R is as defined above.

Representative examples of the cyclic acylurea compounds include hydro-1-hydroxy (or 1-substituted oxy)-1,3,5-triazine-2,6-dione compounds represented by following Formula (2):

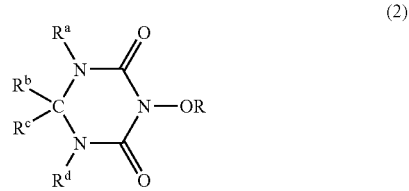

wherein $R^a$ and $R^d$ are the same as or different from each other and each represent hydrogen atom, an alkyl group, an aryl group, a cycloalkyl group, a protected or unprotected hydroxyl group, a protected or unprotected carboxyl group, or an acyl group; $R^b$ and $R^c$ are the same as or different from each other and each represent hydrogen atom, a halogen atom, an alkyl group, an aryl group, a cycloalkyl group, hydroxyl group, an alkoxy group, carboxyl group, a substituted oxycarbonyl group, an acyl group, or an acyloxy group, wherein at least two of $R^a$, $R^b$, $R^c$, and $R^d$ may be combined to form one of a double bond, an aromatic ring, and a non-aromatic ring with an atom constituting the ring in Formula (2), and wherein $R^b$ and $R^c$ may together form an oxo group; and R is as defined above.

The alkyl groups, aryl groups, cycloalkyl groups, and acyl groups as $R^a$ and $R^d$ in Formula (2) are as with the alkyl groups and other groups listed in $R^1$ to $R^6$. The hydroxyl-protecting groups for use herein are as with those mentioned above.

The carboxyl-protecting groups can be conventional protecting groups used in the field of organic synthesis. Examples thereof include alkoxy groups including $C_{1-6}$ alkoxy groups such as methoxy, ethoxy, and butoxy; cycloalkyloxy groups; aryloxy groups such as phenoxy group; aralkyloxy groups such as benzyloxy group; trialkylsilyloxy groups such as trimethylsilyloxy group; substituted or unsubstituted amino groups including amino group and mono- or di-($C_{1-6}$ alkyl)amino groups such as methylamino group and dimethylamino group.

The halogen atoms, alkyl groups, aryl groups, cycloalkyl groups, hydroxyl group, alkoxy groups, carboxyl groups, substituted oxycarbonyl groups, acyl groups, and acyloxy groups as $R^b$ and $R^c$ can be as with the alkyl groups and other substituents listed in $R^1$ to $R^6$.

In Formula (2), at least two of $R^a$, $R^b$, $R^c$, and $R^d$ may be combined to form one of a double bond, an aromatic ring, and a non-aromatic ring with one or more atoms (a carbon atom and/or a nitrogen atom) constituting the ring in Formula (2), and $R^b$ and $R^c$ may together form an oxo group. Preferred aromatic or non-aromatic rings are as with those mentioned above.

Representative examples of preferred cyclic acylurea compounds include compounds each having the skeleton represented by Formula (IIa), such as 3-hydroxyhydantoin, 1,3-dihydroxyhydantoin, 3-hydroxy-1-methylhydantoin, 3-acetoxyhydantoin, 1,3-diacetoxyhydantoin, 3-acetoxy-1-methylhydantoin, 3-benzoyloxyhydantoin, 1,3-bis(benzoyloxy)hydantoin, and 3-benzoyloxy-1-methylhydantoin; compounds each having the skeleton represented by Formula (IIb), such as 4-hydroxy-1,2,4-triazolidine-3,5-dione, 4-hydroxy-1,2-dimethyl-1,2,4-triazolidine-3,5-dione, 4-acetoxy-1,2,4-triazolidine-3,5-dione, 4-acetoxy-1,2-dimethyl-1,2,4-triazolidine-3,5-dione, 4-benzoyloxy-1,2,4-triazolidine-3,5-dione, 4-benzoyloxy-1,2-dimethyl-1,2,4-triazolidine-3,5-dione, 4-hydroxy-1,2,4-triazoline-3,5-dione, 4-acetoxy-1,2,4-triazoline-3,5-dione, and 4-benzoyloxy-1,2,4-triazoline-3,5-dione; compounds each having the skeleton represented by Formula (IIc), such as hexahydro-3-hydroxy-1,3-diazine-2,4-dione, hexahydro-1,3-dihydroxy-1,3-diazine-2,4-dione, hexahydro-3-hydroxy-1-methyl-1,3-diazine-2,4-dione, 3-acetoxy-hexahydro-1,3-diazine-2,4-dione, 1,3-diacetoxy-hexahydro-1,3-diazine-2,4-dione, 3-acetoxy-hexahydro-1-methyl-1,3-diazine-2,4-dione, 3-benzoyloxy-hexahydro-1,3-diazine-2,4-dione, 1,3-bis(benzoyloxy)-hexahydro-1,3-diazine-2,4-dione, 3-benzoyloxy-hexahydro-1-methyl-1,3-diazine-2,4-dione, hexahydro-1-hydroxy-1,3-diazine-2,4,6-trione, 1-acetoxy-hexahydro-1,3-diazine-2,4,6-trione, 1-benzoyloxy-hexahydro-1,3-diazine-2,4,6-trione, hexahydro-1,3-dihydroxy-1,3-diazine-2,4,6-trione, 1,3-diacetoxy-hexahydro-1,3-diazine-2,4,6-trione, 1,3-bis(benzoyloxy)-hexahydro-1,3-diazine-2,4,6-trione, 3-hydroxyuracil, 3-acetoxyuracil, and 3-benzoyluracil; compounds each having the skeleton represented by Formula (IId), such as hexahydro-4-hydroxy-1,2,4-triazine-3,5-dione, hexahydro-4-hydroxy-1,2-dimethyl-1,2,4-triazine-3,5-dione, 4-acetoxy-hexahydro-1,2,4-triazine-3,5-dione, 4-acetoxy-hexahydro-1,2-dimethyl-1,2,4-triazine-3,5-dione, 4-benzoyloxy-hexahydro-1,2,4-triazine-3,5-dione, and 4-benzoyloxy-hexahydro-1,2-dimethyl-1,2,4-triazine-3,5-dione; compounds each having the skeleton represented by Formula (IIe) [including the compounds represented by Formula (2)], such as hexahydro-1,3,5-trihydroxy-1,3,5-triazine-2,4,6-trione, 1,3,5-triacetoxy-hexahydro-1,3,5-triazine-2,4,6-trione, 1,3,5-tris(benzoyloxy)-hexahydro-1,3,5-triazine-2,4,6-trione, hexahydro-1,3,5-tris(methoxymethyloxy)-1,3,5-triazine-2,4,6-trione, hexahydro-1-hydroxy-1,3,5-triazine-2,6-dione, hexahydro-1-hydroxy-3,5-dimethyl-1,3,5-triazine-2,6-dione, 1-acetoxy-hexahydro-1,3,5-triazine-2,6-dione, 1-acetoxy-hexahydro-3,5-dimethyl-1,3,5-triazine-2,6-dione, 1-benzoyloxy-hexahydro-1,3,5-triazine-2,6-dione, and 1-benzoyloxy-hexahydro-3,5-dimethyl-1,3,5-triazine-2,6-dione; and compounds each having the skeleton represented by Formula (IIf), such as hexahydro-5-hydroxy-1,2,3,5-tetrazine-4,6-dione, hexahydro-5-hydroxy-1,2,3-trimethyl-1,2,3,5-tetrazine-4,6-dione, 5-acetoxy-hexahydro-1,2,3,5-tetrazine-4,6-dione, 5-acetoxy-hexahydro-1,2,3-trimethyl-1,2,3,5-tetrazine-4,6-dione, 5-benzoyloxy-hexahydro-1,2,3,5-tetrazine-4,6-dione, and 5-benzoyloxy-hexahydro-1,2,3-trimethyl-1,2,3,5-tetrazine-4,6-dione.

Of the nitrogen-containing cyclic compounds, compounds wherein X is an —OR group and R is hydrogen atom (N-hydroxy cyclic compounds) can be prepared according to a known procedure or a combination of such procedures. Of the nitrogen-containing cyclic compounds, compounds wherein X is an —OR group and R is a hydroxyl-protecting group can be prepared by introducing a desired protecting group into a corresponding compound wherein R is hydrogen atom (N-hydroxy cyclic compound) using a conventional reaction for introducing protecting groups.

More specifically, of the cyclic imide compounds, compounds wherein X is an —OR group and R is hydrogen atom (N-hydroxy cyclic imide compounds) can be prepared by a conventional imidization process such as a process that comprises the steps of allowing a corresponding acid anhydride to react with hydroxylamine for ring-opening of an acid anhydride group, and closing the ring to form an imide. For example, N-acetoxyphthalimide can be prepared by allowing N-hydroxyphthalimide to react with acetic anhydride or to react with an acetyl halide in the presence of a base. These compounds can also be prepared by other processes.

Particularly preferred imide compounds include N-hydroxyimide compounds derived from aliphatic polycarboxylic anhydrides (cyclic anhydrides) or aromatic polycarboxylic anhydrides (cyclic anhydrides), such as N-hydroxysuccinimide, N-hydroxyphthalimide, N,N'-dihydroxypyromellitic diimide, N-hydroxyglutarimide, N-hydroxy-1,8-naphthalenedicarboximide, and N,N'-dihydroxy-1,8;4,5-naphthalenetetracarboxylic diimide; and compounds derived from the N-hydroxyimide compounds by introduction of a protecting group into a hydroxyl group thereof.

Among the cyclic acylurea compounds, 1,3,5-triacetoxy-hexahydro-1,3,5-triazine-2,4,6-trione (i.e., 1,3,5-triacetoxy-isocyanuric acid), for example, can be prepared by allowing hexahydro-1,3,5-trihydroxy-1,3,5-triazine-2,4,6-trione (i.e., 1,3,5-trihydroxyisocyanuric acid) to react with acetic anhydride or to react with an acetyl halide in the presence of a base.

Each of the nitrogen-containing cyclic compounds having the skeleton represented by Formula (i) as a constitutive member of their ring can be used alone or in combination in the reaction. For example, a cyclic imide compound having the cyclic imide skeleton represented by Formula (I) and a cyclic acylurea compound having the cyclic acylurea skeleton represented by Formula (II) can be used in combination. The catalytic nitrogen-containing cyclic compounds A can be formed in the reaction system. The catalytic nitrogen-containing cyclic compounds A can be used in the form of being supported by a carrier. The carrier is often a porous carrier such as activated carbon, zeolite, silica, silica-alumina, or bentonite. The amount of the nitrogen-containing cyclic compounds supported by the carrier is, for example, about 0.1 to about 50 parts by weight, preferably about 0.5 to about 30 parts by weight, and more preferably about 1 to about 20 parts by weight, to 100 parts by weight of the carrier.

The amount of catalytic nitrogen-containing cyclic compounds A can be selected within a broad range, but is preferably such that the proportional ratio of the catalytic nitrogen-containing cyclic compound A to the substrate aromatic compound B in the reaction system (molar ratio; former/latter) is 0.01 or more, preferably 0.05 or more, more preferably 0.1 or more, and especially preferably 0.12 or more, from the viewpoints of the catalytic activity and stability of the catalyst. The upper limit of the proportional ratio of the catalytic nitrogen-containing cyclic compound A to the substrate aromatic compound B in the reaction system (molar ratio; former/latter) is preferably about 100, more preferably about 50, and especially preferably about 20, for satisfactory cost efficiency and operability in aftertreatment. If the proportional ratio of the catalytic nitrogen-containing cyclic compound A to the substrate aromatic compound B in the reaction system (molar ratio; latter/latter) is excessively low, the catalyst may often become unstable, the production of the target compound per a predetermined amount of the catalyst may decrease, often resulting in decreased yield and productivity of the target compound. The proportion of the catalytic nitrogen-containing cyclic compound A in the reaction system in calculation of the proportional ratio is on the basis of fed amount.

[Promoter (Co-Catalyst)]

A promoter (co-catalyst) can be used in combination with the catalytic nitrogen-containing cyclic compound A in the present invention. Such promoters include metallic compounds. The combination use of the catalytic nitrogen-containing cyclic compound A with a metallic compound can improve the rate and selectivity of the reaction.

Metallic elements constituting the metallic compounds are not specifically limited and are often metallic elements of Groups 2 to 15 of the Periodic Table of Elements. The term "metallic element" as used herein also includes boron (B). Preferred metallic elements include transition metal elements (elements of Groups 3 to 12 of the Periodic Table of Elements). Among them, Mn, Co, Zr, Ce, Fe, V, and Mo are preferred, of which Mn and Co are particularly preferred. The valency of the metallic element is not specifically limited and is from about 0 to about 6 in many cases.

Such metallic compounds include, but are not limited to, elementary substances, hydroxides, oxides (including complex oxides), halides (fluorides, chlorides, bromides, and iodides), salts of oxoacids (e.g., nitrates, sulfates, phosphates, borates, and carbonates), salts of isopoly acids, salts of heteropoly acids, and other inorganic compounds of the aforementioned metallic elements; and salts of organic acids (e.g., acetates, propionates, prussiates, naphthenates, and stearates), complexes, and other organic compounds of the metallic elements. Ligands constituting the complexes include OH (hydroxo), alkoxys such as methoxy, ethoxy, propoxy, and butoxy, acyls such as acetyl and propionyl, alkoxycarbonyls such as methoxycarbonyl and ethoxycarbonyl, acetylacetonato, cyclopentadienyl group, halogen atoms such as chlorine and bromine, CO, CN, oxygen atom, $H_2O$ (aquo), phosphorus compounds including phosphines such as triphenylphosphine and other triarylphosphines, $NH_3$ (ammine), NO, $NO_2$ (nitro), $NO_3$ (nitrato), ethylenediamine, diethylenetriamine, pyridine, phenanthroline, and other nitrogen-containing compounds.

Specific examples of metallic compounds include, by taking cobalt compounds as an example, divalent or trivalent cobalt compounds including inorganic compounds such as cobalt hydroxide, cobalt oxide, cobalt chloride, cobalt bromide, cobalt nitrate, cobalt sulfate, and cobalt phosphate; salts of organic acids, such as cobalt acetate, cobalt naphthenate, and cobalt stearate; and complexes such as cobalt acetylacetonate. Illustrative vanadium compounds include, but are not limited to, divalent, trivalent, tetravalent, and pentavalent vanadium compounds including inorganic compounds such as vanadium hydroxide, vanadium oxide, vanadium chloride, vanadyl chloride, vanadium sulfate, vanadyl sulfate, and sodium vanadate; and complexes such as vanadium acetylacetonate, and vanadyl acetylacetonate. Examples of compounds of the other metallic elements include compounds corresponding to the above-mentioned cobalt or vanadium compounds. Each of these metallic compounds can be used alone or in combination. In particular, a combination of a cobalt compound and a manganese compound often remarkably improves the reaction rate. Two or more metallic compounds having different valences, such as a divalent metallic compound and a trivalent metallic compound, are also preferably used in combination.

The total amount of metallic compounds is, for example, about 0.001 to about 10 moles, preferably about 0.01 to about 8 moles, more preferably about 0.1 to about 5 moles, and particularly preferably about 0.5 to about 4 moles, per 1 mole of the catalytic nitrogen-containing cyclic compound A. From the viewpoints of maintaining the activity as the promoter and the stability of the catalytic nitrogen-containing cyclic compound A, the total amount of the metallic compounds is preferably such that the proportional ratio of the metallic compounds to the substrate aromatic compound B (molar ratio; former/latter) in the reaction system is 0.05 or more, preferably 0.1 or more, more preferably 0.2 or more, and particularly preferably 0.3 or more. The upper limit of the proportional ratio of the metallic compounds to the substrate aromatic compound B (molar ratio; former/latter) in the reaction system is preferably about 50, more preferably about 25, and particularly preferably about 10, for satisfactory cost efficiency and operability in aftertreatment. If the amount of the metallic compounds in the reaction system is excessively small, sufficient catalytic activity may not be obtained, the production of the target compound per a specific amount of the catalytic nitrogen-containing cyclic compound A may decrease, and the yield and productivity of the target compound may often decrease. The proportion of the metallic compounds in the reaction system in calculation of the proportional ratio is on the basis of fed amount.

The promoters for use in the present invention also include organic salts each comprising a polyatomic cation or a polyatomic anion and its counter ion, which polyatomic cation or anion contains a Group 15 or Group 16 element of the Periodic Table of Elements having at least one organic group combined therewith. By using the organic salts as the promoters, the rate and selectivity of the reaction can further be improved. The Group 15 elements include N, P, As, Sb, and Bi, and the Group 16 elements include, for example, O, S, Se, and Te. Preferred elements are N, P, As, Sb, and S, of which N, P, and S are more preferred. Representative examples of the organic salts include organic onium salts including organic ammonium salts such as tetrabutylammonium chloride; organic phosphonium salts such as tetrabutylphosphonium chloride; and organic sulfonium salts such as triethylsulfonium iodide. The amount of the organic salts is, for example, about 0.001 to about 0.1 mole, and preferably about 0.005 to about 0.08 mole, per 1 mole of the nitrogen-containing cyclic compound.

Strong acids such as compounds having a pKa of 2 (25° C.) or less can also be used as the promoters in the present invention. Preferred strong acids include, for example, hydrogen halides, hydrohalogenic acids, sulfuric acid, and heteropolyacids. The amount of the strong acids is, for example, about 0.001 to about 3 moles per 1 mole of the catalytic nitrogen-containing cyclic compound A.

In addition, the promoters for use in the present invention further include a compound having a carbonyl group combined with an electron-withdrawing group. Representative examples of the compounds having a carbonyl group combined with an electron-withdrawing group include hexafluoroacetone, trifluoroacetic acid, pentafluorophenyl ketone, pentafluorophenyl ketone, and benzoic acid. The amount of the compound is, for example, about 0.0001 to about 3 moles per 1 mole of the reaction component (substrate) on the basis of fed amount.

According to the present invention, the reaction system may include a radical generator and/or a radical reaction accelerator. Such components include, but are not limited to, halogens such as chlorine and bromine; peracids such as peracetic acid and m-chloroperbenzoic acid; peroxides including hydroperoxides such as hydrogen peroxide and t-butyl hydroperoxide (TBHP); nitric acid, nitrous acid, and salts of them; nitrogen dioxide; aldehydes such as benzaldehyde, including an aldehyde corresponding to the target compound aromatic carboxylic acid or aromatic carboxylic anhydride. The presence of such a component in the reaction system may promote the reaction. The amount of the component is, for example, about 0.001 to about 3 moles per 1 mole of the catalytic nitrogen-containing cyclic compound A.

[Aromatic Compound B Having an Organic Group Bound at Carbon Atom to its Aromatic Ring]

The aromatic compounds B having one or more hydrocarbon groups alone as substituents on its aromatic ring are used as the reaction components (substrates) in the present invention. By using such a compound as the substrate, a hydrocarbon bound to the aromatic ring is oxidized at the binding site and thereby yields a corresponding aromatic carboxylic acid. The total number of hydrocarbon groups bound to the aromatic ring is about one to about six, and preferably about one to about four. When two or more hydrocarbon groups are bound to the aromatic ring, these hydrocarbon groups may be combined to form a ring with carbon-carbon bond constituting the aromatic ring. Each of the aromatic compounds B as substrates can be used alone or in combination. One or more aromatic compounds other than the aromatic compound B having one or more hydrocarbon groups alone as substituents on its aromatic ring may be fed to the reaction system, in addition to the aromatic compound B. Examples of the other aromatic compounds are compounds corresponding to lower-order oxidized products of the aromatic compound B, such as intermediates or precursors of the target compound aromatic carboxylic acid.

Examples of the aromatic ring include aromatic carbon rings such as benzene ring, naphthalene ring, acenaphthylene ring, phenanthrene ring, anthracene ring, and pyrene ring; and aromatic heterocyclic rings each having about one to about three hetero atoms selected from oxygen atom, sulfur atom and nitrogen atom, such as furan ring, thiophene ring, pyrrole ring, pyrazole ring, imidazole ring, tetrazole ring, oxazole ring, isoxazole ring, isothiazole ring, thiazole ring, pyridine ring, 4-oxo-1,4-dihydropyridine ring, 2-oxo-1,2-dihydropyridine ring, pyridazine ring, pyrimidine ring, pyrazine ring, quinoline ring, 4-oxo-4H-pyran ring, 2-oxo-2H-pyran ring, benzofuran ring, indole ring, indazole ring, benzotriazole ring, quinazoline ring, phthalazine ring, 1,8-naphthyridine ring, acridine ring, phenazine ring, and chromone ring.

The hydrocarbon groups bound to the aromatic ring include, for example, aliphatic hydrocarbon groups, alicyclic hydrocarbon groups, aromatic hydrocarbon groups, and groups each comprising these groups combined.

Representative examples of the aliphatic hydrocarbon groups are alkyl groups and alkenyl groups. Examples of the alkyl groups include primary or secondary alkyl groups such as methyl, ethyl, propyl, isopropyl, butyl, isobutyl, s-butyl, pentyl, isopentyl, hexyl, isohexyl, heptyl, octyl, 2-ethylhexyl, and decyl group. Among them, $C_{1-4}$ alkyl groups are preferred, of which $C_{1-3}$ alkyl groups such as methyl group, ethyl group, and isopropyl group are more preferred. The alkenyl groups include $C_{1-4}$ alkenyl groups such as allyl group.

Examples of the alicyclic hydrocarbon groups include cycloalkyl groups having about three to about fifteen members, such as cyclopropyl, cyclobutyl, cyclopentyl, and cyclohexyl groups; and cycloalkenyl groups having about three to about fifteen members, such as cyclohexenyl group.

The aromatic hydrocarbon groups include, for example, phenyl group and naphthyl group. Groups comprising an aliphatic hydrocarbon group combined with an alicyclic hydrocarbon group include cyclopentylmethyl, and cyclohexylmethyl groups. Groups comprising an aliphatic hydrocarbon group combined with an aromatic hydrocarbon group include aralkyl groups such as benzyl and 2-phenylethyl groups.

At least one of hydrocarbon groups bound to the aromatic ring is preferably an aliphatic hydrocarbon group, an alicyclic hydrocarbon group, or an aralkyl group. The aromatic compounds each having one or more hydrocarbon groups bound to the aromatic ring are typically preferably aromatic compounds each having at least one alkyl group bound to their aromatic ring.

Representative examples of the aromatic compounds B having an organic group bound at carbon atom to the aromatic ring include compounds each having one alkyl group bound to the aromatic ring, such as toluene, ethylbenzene, isopropylbenzene (cumene), n-propylbenzene, 1-methylnaphthalene, 2-methylnaphthalene, methylanthracene, 2-methylfuran, 3-methylfuran, 2-methylthiophene, 3-methylthiophene, 2-methylpyridine (α-picoline), 3-methylpyridine (β-picoline), 4-methylpyridine (γ-picoline), 2-ethylpyridine, 3-ethylpyridine, 4-ethylpyridine, 3-isopropylpyridine, 4-methylindole, 5-methylindole, 7-methylindole, 2-methylquinoline, 3-methyl-4-pyrone, and 3-methyl-4-pyridone; compounds each having two alkyl groups bound to the aromatic ring, such as o-xylene, m-xylene, p-xylene, 1-ethyl-4-methylbenzene, 1-ethyl-3-methylbenzene, diisopropylbenzene, 1,5-dimethylnaphthalene, 2,5-dimethylnaphthalene, diisopropylnaphthalene, dimethylanthracene, 4,4'-dimethylbiphenyl, 2,3-dimethylpyridine (2,3-lutidine), 2,4-dimethylpyridine (2,4-lutidine), 2,5-dimethylpyridine (2,5-lutidine), 3,5-dimethylpyridine (3,5-lutidine), 2,6-dimethylpyridine (2,6-lutidine), 2-ethyl-4-methylpyridine, 3,5-dimethyl-4-pyrone, and 3,5-dimethyl-4-pyridone; and compounds each having three or more alkyl groups bound to the aromatic ring, such as 1,2,3-trimethylbenzene, 1,2,4-trimethylbenzene (pseudocumene), 1,3,5-trimethylbenzene (mesitylene), 1,2,3,5-tetramethylbenzene, 1,2,3,4-tetramethylbenzene, 1,2,4,5-tetramethylbenzene (durene), 1,2,3,4,5,6-hexamethylbenzene, trimethylanthracene, 2,3,4-trimethylpyridine, 2,3,5-trimethylpyridine, 2,3,6-trimethylpyridine, 2,4,6-trimethylpyridine, and N,3,5-trimethyl-4-pyridone.

Examples of the compounds which may be fed to the reaction system in addition to the aromatic compound B and which correspond to lower-order oxidized products of the aromatic compound B, such as intermediates or precursors of the target compound aromatic carboxylic acid, include aromatic compounds each having, for example, a hydroxyalkyl group such as hydroxymethyl group, or an acyl group such as formyl group or acetyl group bound to their aromatic ring; and aromatic compounds each having a carboxyl group together with, for example, a hydrocarbon group such as an alkyl group; a hydroxyalkyl group such as hydroxymethyl group; and/or an acyl group such as formyl group or acetyl group bound to their aromatic ring. More specific examples of these compounds are, by taking p-xylene as the aromatic compound B as an example, p-tolualdehyde, p-toluic acid, terephthalaldehyde, and 4-carboxybenzaldehyde.

The production method of the present invention efficiently oxidizes one or more hydrocarbon groups bound to the aromatic ring, such as alkyl groups, into carboxyl groups to thereby yield a corresponding aromatic carboxylic acid (monocarboxylic acid or polycarboxylic acid). For example, the method efficiently yields benzoic acid from toluene, ethylbenzene, isopropylbenzene, or mixture of these; terephthalic acid from p-xylene, p-isopropyltoluene, p-diisopropylbenzene, or a mixture of these; isophthalic acid from m-xylene; trimellitic acid from pseudocumene; pyromellitic acid from durene; and 3-quinolinecarboxylic acid typically from 3-methylquinoline, respectively. The method also yields nicotinic acid from β-picoline. When a compound corresponding to a lower-order oxidized product of the aromatic compound B is added to the reaction system in addition to the aromatic compound B, the compound corresponding to the lower-order oxidized product is further oxidized and is converted into the target compound.

The present invention can efficiently oxidize plural hydrocarbon groups, such as alkyl groups, if bound to the aromatic ring, and is thereby advantageous for the production of aromatic polycarboxylic acids.

[Oxygen]

The oxygen can be molecular oxygen. The molecular oxygen is not specifically limited and can be any of pure oxygen; oxygen diluted with an inert gas such as nitrogen, helium, argon, or carbon dioxide; air; and diluted air. The oxygen can be formed within the reaction system. The oxygen to be fed to the reaction system is preferably an oxygen-containing gas containing oxygen in an amount of, for example, about 5% to about 80%, preferably about 10% to about 50%, and more preferably about 15% to about 25%. The amount of oxygen to be fed can be appropriately selected within a range not adversely affecting, for example, the reactivity, operability, production efficiency, utilization efficiency of catalyst, and safety. The amount is preferably such that the oxygen concentration in the offgas is about 1% to about 8%, and particularly preferably about 3% to about 6%. The production efficiency of the target compound, and the utilization efficiency of the catalyst may often decrease under conditions of an excessively low oxygen concentration in the offgas. In contrast, the safety may often decrease under conditions of an excessively high oxygen concentration in the offgas.

[Reaction]

Important features of the method according to the present invention are (1) employing a continuous gas-liquid reaction system (full circulation system) for maintaining the system to a constant condition by continuously feeding the catalytic nitrogen-containing cyclic compound A, the aromatic compound B, a reaction solvent, and oxygen to a reactor and continuously extracting the reaction mixture from the reactor; and (2) carrying out a reaction under the condition of a concentration of the aromatic compound B in the reaction system of 3.0 percent by weight or less. When the inside of the reactor is not fully homogenous and the concentration has a gradient, the reaction is carried out under such a condition that the concentration of the aromatic compound B is 3.0 percent by weight or less at a point where the concentration of the aromatic compound B stands highest. If the reaction is carried out at a concentration of the aromatic compound B exceeding 3.0 percent by weight, the yield of the target compound significantly decrease, and the production of the target compound per a specific amount of the catalyst used markedly decrease. This is probably because the stability of the catalyst decreases. The concentration of the aromatic compound B in the reaction system is preferably 2.5 percent by weight or less, more preferably 2.0 percent by weight or less, and particularly preferably 1 percent by weight or less (for example, 0.5 percent by weight or less). The concentration of the aromatic compound B in the reaction system can be set in consideration of the reaction rate by adjusting, for example, the reaction temperature, the reaction pressure, the concentration of the aromatic compound B in a fed liquid, the fed amount a compound corresponding to a lower-order oxidized product of the aromatic compound B, if fed to the reaction system, or the recycled amount of the lower-order oxidized product formed as a result of reaction, if recycled to the reaction system, and/or the residence time.

In a batch reaction system [a full batch reaction system or a gas-circulation batch reaction system (a system of continuously feeding gas to the reactor)], when the concentration of the aromatic compound B in the fed liquid is increased, the concentration of the aromatic compound B in the reaction system generally exceeds 3.0 percent by weight in early stages of the reaction to probably reduce the stability of the catalyst, and the reaction rate significantly decreases after the reaction proceeds to some extent. As a result, the yield of the target compound decreases, and the production of the target compound per a specific amount of the used catalyst markedly decreases. In contrast, when the concentration of the aromatic compound B in the fed liquid is decreased, the production of the target compound per one batch is small, and the production efficiency markedly decreases in quantity. Consequently, the target aromatic carboxylic acid cannot be industrially efficiently produced according to a batch system.

The reactor for use in the method according to the present invention can be a reactor generally used in a continuous gas-liquid reaction system. For example, the reactor can be a reactor equipped with material feed lines (liquid feed line and oxygen feed line), a reaction-mixture discharge line, an offgas line, and a gas-liquid mixing device such as stirrer, a baffle, or a perforated plate. The oxygen can be fed to the liquid in the reactor typically using a sparger. The reactor can be of any system such as a mixing tank of full mixing type, or a bubble tower.

The method according to the present invention may use a plurality of reactors connected in series and/or in parallel. In a continuous reaction system using reactors arranged in series, if employed, the reaction is carried out under the condition of a concentration of the aromatic compound B in the reaction system of 3.0 percent by weight or less at least in the downstreammost reactor (last reactor).

Examples of the reaction solvent include aromatic hydrocarbons such as benzene; halogenated hydrocarbons such as dichloromethane, chloroform, 1,2-dichloroethane, and dichlorobenzene; alcohols such as t-butanol and t-amyl alcohol; nitrites such as acetonitrile and benzonitrile; organic acids such as acetic acid, propionic acid, butyric acid, isobutyric acid, and hexanoic acid; and amides such as formamide, acetamide, dimethylformamide (DMF), and dimethylacetamide. Each of these solvents can be used in combination as a mixture. Of these solvents, nitrites and protic organic solvents, such as organic acids, are preferred. Particularly preferred solvents are lower fatty acids such as acetic acid, propionic acid, butyric acid, and isobutyric acid.

Water is generally by-produced during the reaction in the method according to the present invention. The water also functions as a reaction solvent. The reaction rate, however, may markedly decrease if water is present in excess. Accordingly, the reaction is preferably carried out under such a condition that the water content of the reaction system is 30 percent by weight or less, preferably 20 percent by weight or less, and more preferably 10 percent by weight or less, based on the total amount of the reaction system.

The catalytic nitrogen-containing cyclic compound A, the aromatic compound B, the reaction solvent, and the promoter, such as a metallic compound, used according to necessity may be fed to the reaction system respectively from different lines. For example, the catalytic nitrogen-containing cyclic compound A and the promoter, such as a metallic compound, may be fed to the reaction system through different lines. Alternatively, two or more of these components may be mixed and the mixture is fed to the reaction system through one line.

The reaction temperature can be appropriately set in view of the rate and selectivity of the reaction, but is preferably about 150° C. or higher, for example, about 150° C. to about 220° C., more preferably about 150° C. to about 200° C., and particularly preferably about 160° C. to about 190° C. An excessively low reaction temperature may invite a low reaction rate and a low conversion, and may thereby often cause a decreased yield of the target compound. In contrast, an excessively high reaction temperature may invite increased side reactions and/or decreased stability of the catalyst.

The reaction can be carried out under normal pressure (atmospheric pressure) or under a pressure (under a load). The reaction pressure is, for example, normal pressure (0.1 MPa) to about 10 MPa, and preferably about 1 MPa to about 8 MPa, but it may be higher than this range.

The residence time (the residence time of liquid in the reaction system) can be appropriately set according to other reaction conditions such as the reaction temperature, can be generally selected within the range from about 0.2 to about 8 hours, and is preferably about 0.5 to about 4 hours, more preferably about 0.5 to about 3 hours, and particularly preferably about 0.6 to about 2 hours. An excessively short residence time may often decrease the yield of the target compound. In contrast, an excessively long residence time may often decrease the space-time yield (STY).

As a result of the reaction, the aromatic compound B having one or more hydrocarbon groups as substituents is oxidized and thereby yields a corresponding aromatic carboxylic acid. For example, terephthalic acid is efficiently produced from p-xylene as the substrate. In this case, by-products such as p-tolualdehyde, p-toluic acid, terephthalaldehyde, and 4-carboxybenzaldehyde may be formed under some conditions. Such by-products include lower-order oxidized products; and intermediates or precursors of the target aromatic carboxylic acid.

After the completion of the reaction, reaction products can be separated and purified by a separation process such as filtration, concentration, distillation, extraction, crystallization, recrystallization, adsorption, or column chromatography, or a combination of these separation processes. The separated reaction intermediates, unreacted raw material (aromatic compound), catalyst, promoter, solvent, and other components may be recycled to the reaction system. The intermediates herein are precursors of the target aromatic carboxylic acid and include, by taking terephthalic acid being the target as an example, p-tolualdehyde, p-toluic acid, terephthalaldehyde, and 4-carboxybenzaldehyde. The solvent, if recycled, may be recycled after removing water in the solvent, which has been by-produced as a result of the reaction, by means of separation or adsorption using a dehydrator.

Resulting aromatic carboxylic acids produced according to the method of the present invention can be used typically as raw materials for polyamides (nylons) and polyester, and intermediates for fine chemicals.

EXAMPLES

The present invention will be illustrated in further detail with reference to several EXAMPLES below, which by no means limit the scope of the present invention.

Example 1

A reaction was carried out according to a continuous gas-liquid reaction system in a reactor equipped with a reflux condenser, a stirrer, a mass flow unit, a material feed line, a gas inlet line, a reaction-mixture extraction line, an offgas line, a pressure gauge, and a pressure adjuster. Specifically, into the reactor was continuously fed an acetic acid mixture containing 10 percent by weight of p-xylene, 0.60 percent by weight of N-hydroxynaphthalimide (N-hydroxy-1,8-naphthalenedicarboximide) (3 percent by mole with respect to the charged p-xylene), 0.23 percent by weight of manganese(II) acetate tetrahydrate, and 0.09 percent by weight of cobalt(II) acetate tetrahydrate; air was continuously introduced into the reactor through its bottom so that the oxygen concentration in the offgas line was 3% to 6%; the reaction was carried out under conditions of a reaction temperature 170° C., a reaction pressure of 2 MPa, a residence time of one hour, and a p-xylene concentration of the reaction system in a steady state of 0.09 percent by weight; and the reaction mixture was continuously discharged out of the reaction system. The discharged reaction mixture was analyzed by high-performance liquid chromatography to find that terephthalic acid was produced in a yield of 83.4% with a conversion from p-xylene of 99.1%. The ratio of N-hydroxynaphthalimide (on the basis of fed amount) to p-xylene (former/latter; molar ratio) in the reaction system in a steady state was 3.3. The production of terephthalic acid was 27.8 moles per 1 mole of the catalyst (N-hydroxynaphthalimide) (1.83 times as much as that in following COMPARATIVE EXAMPLE 1).

Comparative Example 1

A reaction was carried out according to a gas circulation batch reaction system in a reactor equipped with a reflux condenser, a stirrer, a mass flow unit, a gas inlet line, an offgas line, a pressure gauge, and a pressure adjuster. Specifically, 380 g of an acetic acid mixture containing 10 percent by weight of p-xylene, 0.60 percent by weight of N-hydroxynaphthalimide(N-hydroxy-1,8-naphthalenedicarboximide) (3 percent by mole with respect to fed p-xylene), 0.23 percent by weight of manganese(II) acetate tetrahydrate, 0.09 percent by weight of cobalt(II) acetate tetrahydrate was placed in the reactor. The reaction was carried out at a reaction temperature 170° C. and a reaction pressure of 2 MPa for two hours while feeding air to the reactor through its bottom at a flow rate of 200 NL/h. After cooling, the reaction mixture was analyzed by high-performance liquid chromatography to find that terephthalic acid was produced in a yield of 45.5% with a conversion from p-xylene of 96.5%. The p-xylene concentration in the reaction system was 10 percent by weight at the beginning of the reaction and was 0.35 percent by weight upon the completion of the reaction. The ratio of N-hydroxynaphthalimide (on the basis of fed amount) to p-xylene (former/latter; molar ratio) in the reaction system was 0.03 at the beginning of the reaction and was 0.86 upon the completion of the reaction. The production of terephthalic acid was 15.2 moles per 1 mole of the catalyst (N-hydroxynaphthalimide).

Another reaction was carried out under the same conditions as above, except for carrying out the reaction for five hours, to find that the yield of terephthalic acid was 47.4%, merely slightly higher than that in the above-mentioned reaction carried out for two hours.

Example 2

A reaction was carried out by the procedure of EXAMPLE 1, except for using, instead of N-hydroxynaphthalimide, 3 percent by mole of N-acetoxynaphthalimide (N-acetoxy-1,8-naphthalenedicarboximide) with respect to fed p-xylene. The p-xylene concentration in the reaction system in a steady state was 0.15 percent by weight. The obtained reaction mixture was analyzed by high-performance liquid chromatography to find that terephthalic acid was produced in a yield of 80.9% with a conversion from p-xylene of 98.5%. The ratio of N-acetoxynaphthalimide (on the basis of fed amount) to p-xylene (former/latter; molar ratio) in the reaction system in a steady state was 2.0. The production of terephthalic acid was 27.0 moles per 1 mole of the catalyst (N-acetoxynaphthalimide) (1.52 times as much as that in following COMPARATIVE EXAMPLE 2).

Comparative Example 2

A reaction was carried out by the procedure of COMPARATIVE EXAMPLE 1, except for using, instead of N-hydroxynaphthalimide, 3 percent by mole of N-acetoxynaphthalimide(N-acetoxy-1,8-naphthalenedicarboximide) with respect to fed p-xylene. The reaction mixture was analyzed by high-performance liquid chromatography to find that terephthalic acid was produced in a yield of 53.5% with a conversion from p-xylene of 98.5%. The p-xylene concentration in the reaction system was 10 percent by weight at the beginning of the reaction and was 0.15 percent by weight upon the completion of the reaction. The ratio of N-acetoxynaphthalimide (on the basis of fed amount) to p-xylene (former/latter; molar ratio) in the reaction system was 0.03 at the beginning of the reaction and was 2 upon the completion of the reaction. The production of terephthalic acid was 17.8 moles per 1 mole of the catalyst (N-acetoxynaphthalimide).

Another reaction was carried out under the same conditions as above, except for carrying out the reaction for five hours, to find that the yield of terephthalic acid was 58.0%, merely slightly higher than that in the above-mentioned reaction carried out for two hours.

Example 3

A reaction was carried out by the procedure of EXAMPLE 1, except for using, instead of N-hydroxynaphthalimide, 3 percent by mole of N-acetoxyphthalimide with respect to fed p-xylene. The p-xylene concentration in the reaction system in a steady state was 0.66 percent by weight. The obtained reaction mixture was analyzed by high-performance liquid chromatography to find that terephthalic acid was produced in a yield of 45.4% with a conversion from p-xylene of 93.4%. The ratio of N-acetoxyphthalimide (on the basis of fed amount) to p-xylene (former/latter; molar ratio) in the reaction system in a steady state was 0.45. The production of terephthalic acid was 15.1 moles per 1 mole of the catalyst (N-acetoxyphthalimide) (2.60 times as much as that in following COMPARATIVE EXAMPLE 3).

Comparative Example 3

A reaction was carried out by the procedure of COMPARATIVE EXAMPLE 1, except for using, instead of N-hydroxynaphthalimide, 3 percent by mole of N-acetoxyphthalimide with respect to fed p-xylene. The reaction mixture was analyzed by high-performance liquid chromatography to find that terephthalic acid was produced in a yield of 17.5% with a conversion from p-xylene of 97.8%. The p-xylene concentration in the reaction system was 10 percent by weight at the beginning of the reaction and was 0.22 percent by weight upon the completion of the reaction. The ratio of N-acetoxyphthalimide (on the basis of fed amount) to p-xylene (former/latter; molar ratio) in the reaction system in a steady state was 0.03 at the beginning of the reaction and was 1.4 upon the completion of the reaction. The production of terephthalic acid was 5.8 moles per 1 mole of the catalyst (N-acetoxyphthalimide).

Example 4

A reaction was carried out by the procedure of EXAMPLE 1, except for using, instead of N-hydroxynaphthalimide, 3 percent by mole of N-acetoxysuccinimide (N-acetoxysuccinimide) with respect to fed p-xylene. The p-xylene concentration in the reaction system in a steady state was 0.23 percent by weight. The obtained reaction mixture was analyzed by high-performance liquid chromatography to find that terephthalic acid was produced in a yield of 68.0% with a conversion from p-xylene of 97.7%. The ratio of N-acetoxysuccinimide (on the basis of fed amount) to p-xylene (former/latter; molar ratio) in the reaction system in a steady state was 1.3. The production of terephthalic acid was 22.7 moles per 1 mole of the catalyst (N-acetoxysuccinimide).

Example 5

A reaction was carried out by the procedure of EXAMPLE 1, except for using, instead of N-hydroxynaphthalimide, 3 percent by mole of N-hydroxysuccinimide (N-hydroxysuccinimide) with respect to fed p-xylene. The p-xylene concentration in the reaction system in a steady state was 0.22 percent by weight. The obtained reaction mixture was analyzed by high-performance liquid chromatography to find that terephthalic acid was produced in a yield of 70.5% with a conversion from p-xylene of 97.8%. The ratio of N-hydroxysuccinimide (on the basis of fed amount) to p-xylene (former/latter; molar ratio) in the reaction system in a steady state was 1.4. The production of terephthalic acid was 23.5 moles per 1 mole of the catalyst (N-hydroxysuccinimide).

Example 6

A reaction was carried out by the procedure of EXAMPLE 1, except for using, instead of N-hydroxynaphthalimide, 1 percent by mole of N,N',N''-triacetoxyisocyanuric acid (1,3,5-triacetoxyisocyanuric acid) with respect to fed p-xylene. The p-xylene concentration in the reaction system in a steady state was 0.15 percent by weight. The obtained reaction mixture was analyzed by high-performance liquid chromatography to find that terephthalic acid was produced in a yield of 68.0% with a conversion from p-xylene of 98.5%. The ratio of N,N',N''-triacetoxyisocyanuric acid (on the basis of fed amount) to p-xylene (former/latter; molar ratio) in the reaction system in a steady state was 0.67. The production of terephthalic acid was 68.0 moles per 1 mole of the catalyst (N,N',N''-triacetoxyisocyanuric acid).

Example 7

A reaction was carried out by the procedure of EXAMPLE 1, except for using 1 percent by mole of N-hydroxynaphthalimide with respect to fed p-xylene. The p-xylene concentration in the reaction system in a steady state was 0.44 percent by weight. The obtained reaction mixture was analyzed by high-performance liquid chromatography to find that terephthalic acid was produced in a yield of 55.8% with a conversion from p-xylene of 95.6%. The ratio of N-hydroxynaphthalimide (on the basis of fed amount) to p-xylene (latter/latter; molar ratio) in the reaction system in a steady state was 0.23. The production of terephthalic acid was 55.8 moles per 1 mole of the catalyst (N-hydroxynaphthalimide).

Example 8

Two-Step Reaction

N-Hydroxynaphthalimide was added to the reaction mixture obtained in EXAMPLE 6 to a content of 0.2 percent by weight. The procedure of EXAMPLE 4 was conducted, except for feeding the resulting mixture to the reactor. The p-xylene concentration in the reaction system in a steady state was 0.005 percent by weight or less. The obtained reaction mixture was analyzed by high-performance liquid chromatography to find that terephthalic acid was produced in a yield (total yield) of 88% with a conversion from p-xylene of 100%.

Example 9

A reaction was carried out by the procedure of EXAMPLE 1, except for setting the residence time at 0.5 hour and the p-xylene concentration in the reaction system in a steady state at 0.5 percent by weight. The obtained reaction mixture was analyzed by high-performance liquid chromatography to find that terephthalic acid was produced in a yield of 60% with a conversion from p-xylene of 95%. The ratio of N-hydroxynaphthalimide (on the basis of fed amount) to p-xylene (latter/latter; molar ratio) in the reaction system in a steady state was 0.6. The production of terephthalic acid was 20 moles per 1 mole of the catalyst (N-hydroxynaphthalimide).

Example 10

A reaction was carried out by the procedure of EXAMPLE 1, except for setting the residence time at 2 hours and the p-xylene concentration in the reaction system in a steady state at 0.1 percent by weight. The obtained reaction mixture was analyzed by high-performance liquid chromatography to find that terephthalic acid was produced in a yield of 90% with a conversion from p-xylene of 99%. The ratio of N-hydroxynaphthalimide (on the basis of fed amount) to p-xylene (latter/latter; molar ratio) in the reaction system in a steady state was 3.0. The production of terephthalic acid was 30 moles per 1 mole of the catalyst (N-hydroxynaphthalimide).

Example 11

A reaction was carried out by the procedure of EXAMPLE 1, except for setting the residence time at 4 hours and the p-xylene concentration in the reaction system in a steady state at 0.08 percent by weight. The obtained reaction mixture was analyzed by high-performance liquid chromatography to find that terephthalic acid was produced in a yield of 93% with a conversion from p-xylene of 99.2%. The ratio of N-hydroxynaphthalimide (on the basis of fed amount) to p-xylene (latter/latter; molar ratio) in the reaction system in a steady state was 3.8. The production of terephthalic acid was 31 moles per 1 mole of the catalyst (N-hydroxynaphthalimide).

Example 12

A reaction was carried out by the procedure of EXAMPLE 1, except for setting the reaction temperature at 150° C. and the p-xylene concentration in the reaction system in a steady state at 0.8 percent by weight. The obtained reaction mixture was analyzed by high-performance liquid chromatography to find that terephthalic acid was produced in a yield of 60% with a conversion from p-xylene of 92%. The ratio of N-hydroxynaphthalimide (on the basis of fed amount) to p-xylene (latter/latter; molar ratio) in the reaction system in a steady state was 0.38. The production of terephthalic acid was 20 moles per 1 mole of the catalyst (N-hydroxynaphthalimide).

Example 13

A reaction was carried out by the procedure of EXAMPLE 1, except for setting the reaction temperature at 190° C. and the p-xylene concentration in the reaction system in a steady state at 0.2 percent by weight. The obtained reaction mixture was analyzed by high-performance liquid chromatography to find that terephthalic acid was produced in a yield of 83% with a conversion from p-xylene of 98%. The ratio of N-hydroxynaphthalimide (on the basis of fed amount) to p-xylene (latter/latter; molar ratio) in the reaction system in a steady state was 1.5. The production of terephthalic acid was 28 moles per 1 mole of the catalyst (N-hydroxynaphthalimide).

The invention claimed is:
1. A method for producing an aromatic carboxylic acid, by oxidizing an aromatic compound B with oxygen in the presence of a catalytic nitrogen-containing cyclic compound A to thereby yield a corresponding aromatic carboxylic acid,
the aromatic compound B having one or more hydrocarbon groups alone as substituents on its aromatic ring, and the catalytic nitrogen-containing cyclic compound A having a skeleton represented by following Formula (i):

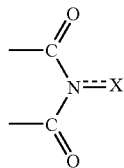

(i)

wherein X represents oxygen atom or an —OR group, and wherein R represents hydrogen atom or a hydroxyl-protecting group, as a constitutive member of its ring, the method comprising the step of carrying out a reaction at:

a concentration of the aromatic compound B in the reaction system of 3.0 percent by weight or less;

a molar ratio of the catalytic nitrogen-containing cyclic compound A to the aromatic compound B in the reaction system of 0.01 or more;

an oxygen concentration in an offgas of 1% to 8% with the oxygen to be fed to the reaction system being an oxygen-containing gas containing oxygen in an amount of 10% to 50%; and a pressure of oxygen to be fed to the reaction system being 0.1 MPa to 4 MPa, while continuously feeding the catalytic nitrogen-containing cyclic compound A, the aromatic compound B, a reaction solvent, and oxygen to a reactor and continuously extracting a reaction mixture from the reactor.

2. The method for producing an aromatic carboxylic acid according to claim 1, wherein the reaction is carried out at a reaction temperature of 150° C. or higher.

3. The method for producing an aromatic carboxylic acid according to claim 1, wherein the reaction is carried out at a residence time of 0.5 to 4 hours.

4. The method for producing an aromatic carboxylic acid according to claim 1, wherein the reaction is continuously carried out using plural reactors arranged in series at a concentration of the aromatic compound B in the reaction system at least in the downstreammost reactor of 3.0 percent by weight or less.

5. The method for producing an aromatic carboxylic acid according to claim 1, wherein the catalytic nitrogen-containing cyclic compound A comprises a cyclic imide compound having a cyclic imide skeleton represented by following Formula (I):

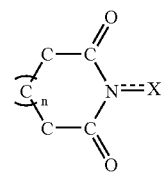

(I)

wherein "n" denotes 0 or 1; and X represents oxygen atom or an —OR group, wherein R represents hydrogen atom or a hydroxyl-protecting group, or a cyclic acylurea compound having a cyclic acylurea skeleton represented by following Formula (II):

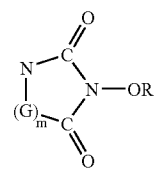

(II)

wherein "m" denotes 1 or 2; G represents carbon atom or nitrogen atom, wherein when m is 2, two Gs may be the same as or different from each other; and R is as defined above.

6. The method for producing an aromatic carboxylic acid according to claim 1, further comprising adding a metallic compound as a promoter.

7. The method for producing an aromatic carboxylic acid according to claim 6, wherein the metallic compound is at least one compound selected from the group consisting of cobalt compounds and manganese compounds.

8. The method for producing an aromatic carboxylic acid according to claim 6, wherein the amount of the metallic compound is 0.001 to 10 moles per 1 mole of the catalytic nitrogen-containing cyclic compound A.

* * * * *